(12) United States Patent
Haberkorn et al.

(10) Patent No.: US 9,016,332 B2
(45) Date of Patent: Apr. 28, 2015

(54) METHOD AND APPARATUS FOR SAFETY-COMPLIANT EMPTYING AND FILLING OF A REAGENT CONTAINER

(75) Inventors: Claus Haberkorn, Dielheim (DE); Hermann Ulbrich, Bad Schönborn (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 588 days.

(21) Appl. No.: 13/273,316

(22) Filed: Oct. 14, 2011

(65) Prior Publication Data

US 2012/0090726 A1    Apr. 19, 2012

(30) Foreign Application Priority Data

Oct. 15, 2010   (DE) .......................... 10 2010 038 215

(51) Int. Cl.
*B65B 1/04*      (2006.01)
*G01N 35/10*    (2006.01)
*G01N 1/31*      (2006.01)

(52) U.S. Cl.
CPC .............. *G01N 35/1002* (2013.01); *G01N 1/31* (2013.01)

(58) Field of Classification Search
CPC .............................. G01N 35/1002; G01N 1/31
USPC .......................... 141/65, 99, 323; 422/63, 73; 604/317–319, 326
See application file for complete search history.

(56) References Cited

U.S. PATENT DOCUMENTS

| | | | | |
|---|---|---|---|---|
| 3,650,698 | A | * | 3/1972 | Adler ............................... 422/73 |
| 3,912,456 | A | * | 10/1975 | Young .............................. 436/47 |
| 5,741,237 | A | * | 4/1998 | Walker .......................... 604/317 |
| 5,939,330 | A | * | 8/1999 | Peterson ....................... 436/180 |
| 7,469,727 | B2 | * | 12/2008 | Marshall ......................... 141/65 |
| 7,806,879 | B2 | * | 10/2010 | Brooks et al. ................. 604/319 |
| 7,829,021 | B2 | * | 11/2010 | Hutchins et al. ................ 422/63 |
| 8,172,817 | B2 | * | 5/2012 | Michaels et al. .............. 604/317 |
| 8,529,548 | B2 | * | 9/2013 | Blott et al. ..................... 604/543 |
| 2010/0055777 | A1 | | 3/2010 | Rapp et al. | |
| 2010/0093073 | A1 | | 4/2010 | Erhardt | |

FOREIGN PATENT DOCUMENTS

| | | |
|---|---|---|
| DE | 28 48 434 | 5/1980 |
| DE | 91 07 077 | 11/1991 |
| DE | 20 2007 013 815 | 1/2008 |
| DE | 10 2008 027 486 | 12/2009 |
| DE | 20 2010 004 275 | 3/2011 |
| GB | 2432669 A | 5/2007 |
| WO | 03/012025 | 2/2003 |
| WO | 2009149691 A2 | 12/2009 |

* cited by examiner

*Primary Examiner* — Timothy L Maust
(74) *Attorney, Agent, or Firm* — Hodgson Russ LLP

(57) ABSTRACT

An apparatus for safety-compliant emptying and filling of a reagent container (24, 40) for a tissue processor (20) comprises a suction line (30, 42) for aspirating a reagent out of the reagent container (24, 40) and a delivery line (32, 44) for filling the reagent container (24, 40) with the reagent, a terminating opening (31, 43) of the suction line (30, 42) being spaced away from a terminating opening (33, 45) of the delivery line (32, 44).

20 Claims, 4 Drawing Sheets

METHOD AND APPARATUS FOR SAFETY-COMPLIANT EMPTYING AND FILLING OF A REAGENT CONTAINER

CROSS REFERENCE TO RELATED APPLICATIONS

This application claims priority of German patent application number 10 2010 038 215.9 filed Oct. 15, 2010, the entire disclosure of which is incorporated by reference herein.

FIELD OF THE INVENTION

The present invention relates generally to automatic processing of tissue specimen, and more particularly to a method and apparatus for emptying and filling of a reagent container.

BACKGROUND OF THE INVENTION

A tissue processor is suitable for processing tissue specimens so that the latter can subsequently be prepared for investigation using a microscope. The tissue specimens are, in particular, embedded with the aid of the tissue processor, for example in paraffin, so that the paraffin block resulting therefrom can be cut with the aid of a microtome into extremely thin sections that can then be investigated using a microscope. Before being embedded in paraffin, the tissue specimens are usually subjected to multiple process steps, for example one or more clearing steps and/or one or more dehydration steps. A variety of reagents, for example formalin, xylene, or alcohol, are required in order to carry out the individual process steps. These reagents are stocked in reagent containers that are arranged, for example, replaceably in the tissue processor.

In the context of automatic processing of tissue specimens using the tissue processor, the reagents are pumped out of the reagent containers into a retort, which is also referred to as a "process chamber" or "bioreactor," and the tissue specimens are exposed to the reagent in the process chamber. Once the individual process steps are complete, the reagents are pumped back into the reagent containers. The reagents can be stocked in reagent containers of various shapes; in particular, the openings of the reagent containers for emptying and filling the reagent containers can be differently configured. The reagents can furthermore encompass ingredients that are hazardous to health, which should not splash out of the reagent containers or evaporate from them into the surroundings of the tissue processor.

The document DE 20 2007 013 815 U1 discloses an apparatus for metered filling of vessels, which apparatus encompasses a suction line and a delivery line that are spaced apart from one another. The suction device and the delivery device are separated from one another and do not open directly into the same vessel. The apparatus is used for filling operations involving powdered material.

The document WO 2003/012025 A2 describes a bioreactor for cultivating cells, in which bioreactor two lines are provided, of which one opens above the liquid level and one in the liquid. The line ending above the liquid level serves to convey in a gas and/or a liquid, and the line ending in the liquid serves for venting.

The document DE 91 07 077 U1 discloses a disposal unit for filling and emptying small containers in underground mining, in which unit two lines are provided whose openings have a spacing from one another. The liquid is conveyed in and aspirated through the first line, while the second line serves as a static tube with which complete filling of the small container can be ascertained.

The document DE 28 48 434 A1 describes a filling adapter for filling a vessel with liquids, which adapter comprises a line for conveying in and aspirating the liquid, the opening of which is adjustable as to height.

The document DE 20 2010 004 275 U1 discloses an apparatus for fuel delivery that encompasses a connector piece for connection to at least one fuel line of an engine.

The document DE 10 2008 027 486 A1 discloses an apparatus for separating tissue cells from a liquid, in which a suction line is used to aspirate the liquid. A bypass line is also provided.

SUMMARY OF THE INVENTION

It is an object of the present invention to create a method and an apparatus for safety-compliant emptying and filling of a reagent container for a tissue processor, which method and apparatus contribute to safety-compliant filling and emptying of the reagent containers.

According to a first aspect, the invention is notable for an apparatus having a suction line for aspirating a reagent out of the reagent container and having a delivery line for filling the reagent container with the reagent, a terminating opening of the suction line being spaced away from a terminating opening of the delivery line.

Because of the separate lines for aspirating the reagent out of the reagent container and for filling the reagent container with the reagent, and because of the spacing of the two terminating openings of the corresponding lines, it is possible to arrange the suction line below a fill level, in particular a maximum fill level, of the reagent in the reagent container, and to arrange the terminating opening of the delivery line above the fill level of the reagent in the reagent container. This makes it possible on the one hand to aspirate the reagent in air- and bubble-free fashion out of the reagent container, and on the other hand to return the reagent into the reagent container without forming bubbles in the reagent container, thereby minimizing splashing of the reagent out of the reagent container because of rising bubbles within the liquid. This is advantageous in particular when, in order to clean the lines, air under pressure is delivered or forced in pulsed fashion through the lines (also referred to as "purging").

The spacing between the two terminating openings is preferably sufficiently large that the terminating opening of the suction line is located close to a bottom of the reagent container, and the terminating opening of the delivery line is located close to an opening of the reagent container or at least above the maximum fill level of the reagent in the reagent container. The spacing can, in particular, be variable, so that the apparatus is adjustable to reagent containers of different sizes and/or to maximum fill levels of different heights.

In an advantageous refinement, the apparatus comprises a coupling member for coupling to the reagent container. A first spacing between the coupling member and the terminating opening of the suction line is greater than a second spacing between the coupling member and the terminating opening of the delivery line. The coupling member allows the opening of the reagent container to be covered, the two lines preferably being guided through the coupling member. It is advantageous in this connection, for reagent containers of different sizes and/or for maximum fill levels of different heights, if the first and/or the second spacing are variable. In this connection, the coupling member can also be referred to as a connector member or as a cover. In particular, the coupling member can be embodied so that it completely covers the opening of the reagent container except for the two lines. The coupling member can, for example, encompass a spherical-segment-shaped part that is provided for placement onto the opening of the reagent container. This allows the opening to be covered reliably even if its diameter and configuration vary from one reagent container to another.

In a further advantageous embodiment, the apparatus encompasses a system line for communication with the process chamber of the tissue processor, and a valve unit communicating with the system line. In a first valve setting, the valve unit enables communication between the system line and the suction line and suppresses communication between the system line and the delivery line. In a second valve position, the valve unit enables communication between the system line and the delivery line and suppresses communication between the system line and the suction line. This makes it possible to provide only one system line that communicates with the process chamber. This can contribute to a simple physical design for the tissue processor in the region of the process chamber.

According to a refinement, the valve unit encompasses at least two valves. In particular, the valve unit can encompass at least four valves, each two of the valves preferably being arranged redundantly. This contributes to ensuring that even in the event of failure of one of the valves, a second respective valve is in place which guarantees proper functionality of the valve unit. It is advantageous if at least one of the valves comprises a wedge-shaped or double-wedge-shaped valve plunger. This enables a low flow resistance and thus a consistently high pumping speed or suction speed at low pressure or suction, respectively; this contributes to a capability for rapid filling of the process chamber with the corresponding reagent, or for rapid pumping of the corresponding reagent back into the reagent container.

A further contribution to rapid filling of the process chamber or reagent container can also be made by arranging and embodying the valves so that in the idle state they are in a closed state. It is particularly advantageous in this context to embody and arrange the valves in such a way that they assume their position in the idle state solely as a result of the action of gravity. This contributes to an ability to keep the opening pressure for opening the valves particularly low, which contributes to rapid filling of the process chamber or reagent container, respectively. The idle state is defined by the fact that it is assumed, inter alia, when no reagent is being aspirated or pumped through the lines and/or through the valve unit.

In an embodiment, the valve unit is encompassed by the coupling member. In other words, the valve unit can be part of the coupling member, in particular of the connector member or the cover. This can in turn contribute to a particularly simple design configuration of the tissue processor.

According to a refinement, the suction line is lance-shaped at least in part, and in other words encompasses a suction lance. In particular, the part of the suction line that protrudes into the reagent container, in particular below the fill level, is lance-shaped. It is possible thereby to ensure that the reagent can be aspirated almost entirely, or entirely, out of the reagent container. Alternatively or additionally, at least a part of the suction line is spiral-shaped, and in other words encompasses a suction spiral. The spiral-shaped part of the suction line is preferably located, when used as intended, outside the reagent container and is arranged in the flow direction between the terminating opening of the suction line (for example, the suction lance) and the coupling member and/or valve unit. For example, the spiral-shaped part of the suction line can be coiled around the valve unit and thus around the coupling member.

It is advantageous in this connection if the apparatus comprises a bypass, in particular a bypass orifice, that enables communication between the spiral-shaped part of the suction line and the delivery line regardless of the valve position of the valve unit; the bypass comprises at least one constriction whose opening cross section is smaller than an opening cross section of the suction line and than an opening cross section of the delivery line. The opening cross section of the constriction is, in particular, substantially smaller than the other two opening cross sections, so that the bypass does not substantially influence the functionality of the valve unit. The bypass allows a portion of the compressed air that is used to deliver the reagent through the delivery line to be used to clean the spiral-shaped and/or lance-shaped part of the suction line, and to minimize carryover and contamination of the reagent.

In a further advantageous embodiment, the apparatus comprises a venting line. The venting line can contribute to minimizing, quickly dissipating, or preventing a negative or positive pressure in the reagent container, which contributes to secure seating of the coupling member on the opening of the reagent container, and to preventing any splashing of reagent out of the reagent container even in the event of pressure pulses in the delivery line. It is particularly advantageous in this connection if the coupling member at least in part encompasses the venting line and a terminating opening of the venting line. Particularly rapid pressure dissipation can be achieved if the terminating opening of the venting line is arranged between the terminating opening of the suction line and the terminating opening of the delivery line, in particular directly and/or particularly close to the delivery line or in fact inside the delivery line, for example close to the terminating opening of the delivery line.

A physical design that is particularly compact and simple can be achieved by the fact that the suction line is arranged at least in part inside the delivery line, the reagent in the delivery line being guided between the inner wall of the delivery line and an outer wall of the suction line.

The formation of bubbles and/or splashes can be prevented if the delivery line encompasses multiple terminating openings and/or if the delivery line is embodied, in the region of the terminating opening of the delivery line, in such a way that when used as intended, it is arranged obliquely with reference to a surface of the reagent in the reagent container. In other words, an axis of the delivery line is configured in the region of the terminating opening so that it forms an angle of between 0° and 90°, preferably between 20° and 70°, with the surface of the liquid reagent in the reagent container.

According to a second aspect, the invention is notable for a method for emptying and filling the reagent container for the tissue processor. In this context, the reagent container is emptied via the suction line and filled via the delivery line, the terminating opening of the delivery line being spaced away from the terminating opening of the suction line.

According to a refinement, the terminating opening of the suction line is arranged below a fill level of the reagent in the reagent container, and the terminating opening of the delivery line is arranged above the maximum fill level of the reagent container.

The method can be carried out in particular using the apparatus for emptying and filling the reagent container, the advantageous configurations, embodiments, and refinements of the apparatus also being transferable to the method.

BRIEF DESCRIPTION OF THE DRAWINGS

Exemplary embodiments of the present invention are described in more detail below with reference to the schematic drawings, in which.

Elements having the same design or function are identified by the same reference numerals throughout the figures.

DETAILED DESCRIPTION OF THE INVENTION

Figure 1:
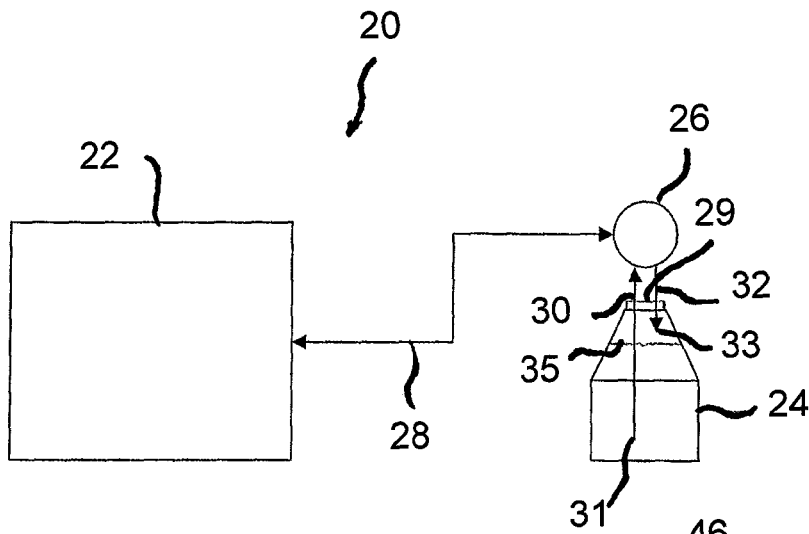
FIG. 1 is a block diagram of a first embodiment of a tissue processor.

FIG. 1 is a block diagram of a tissue processor 20 from which its function may be gathered. Tissue processor 20 is suitable for processing tissue specimens (not depicted), in particular for clearing, dehydrating, and embedding the tissue specimens. Tissue processor 20 encompasses a process chamber 22, which can also be referred to as a retort or bioreactor, for receiving the tissue specimens. Tissue processor 20 further encompasses a first reagent holder 24 and, for emptying and filling reagent container 24, an apparatus that encompasses a first valve unit 26, a system line 28, a first suction line 30, and a first delivery line 32. A cover 29 is preferably provided in order to cover an opening of first reagent container 24.

First valve unit 26 communicates with first reagent container 24 via first suction line 30 and first delivery line 32. A terminating opening 31 of first suction line 30 and a terminating opening 33 of first delivery line 32 are at a predefined spacing, greater than zero, from one another. In particular, during use as intended, terminating opening 31 of first suction line 30 is located below a fill level, in particular a maximum fill level 35, of the reagent in first reagent container 24, and terminating opening 33 of first delivery line 32 is located above the fill level of the reagent. First suction line 30 is preferably embodied so that its terminating opening 31 is arranged close to a bottom of first reagent container 24. First delivery line 32 is preferably embodied so that its terminating opening 33 is arranged close to an opening of first reagent container 24. It is particularly advantageous in this connection if first suction line 30 and/or first delivery line 32 are variable in terms of their length, so that the apparatus is adaptable to first reagent containers 24 of different sizes and/or to maximum fill levels 35 of different heights.

First reagent container 24 is preferably arranged in a special chamber of tissue processor 20, for example in a pull-out compartment of tissue processor 20. As an alternative thereto, first reagent container 24 can also be arranged outside the housing of tissue processor 20 and can communicate with tissue processor 20 only via the lines.

First valve unit 26 comprises at least two valves, with which two valve positions of valve unit 26 can be implemented. In a first valve position, communication is possible between system line 28 and first suction line 30, with the result that the reagent can flow from first suction line 30 into system line 28, communication between system line 28 and first delivery line 32 being suppressed. In a second valve position, communication is possible between system line 28 and first delivery line 32, with the result that the reagent can flow from system line 28 into first delivery line 32, communication between system line 28 and first suction line 30 being suppressed.

In order to aspirate the reagent out of first reagent container 24 and thus in order to empty first reagent container 24, a negative pressure is generated in process chamber 22. The negative pressure in process chamber 22 causes first valve unit 26 to assume the first valve position, so that as a result of the negative pressure in process chamber 22, the reagent is drawn out of first reagent container 24, through first suction line 30, first valve unit 26, and system line 28, into process chamber 22.

In order to fill first reagent container 24 and thus to empty process chamber 22, a positive pressure is generated in process chamber 22, with the result that first valve unit 26 assumes the second valve position and the reagent is delivered out of process chamber 22, through system line 28, first valve unit 26, and first delivery line 32, back into reagent container 24. For complete emptying of system line 28, it is advantageous, at the end of the operation of filling first reagent container 24, to close a valve (not depicted) on system line 28 and to generate a strong positive pressure in process chamber 22. Once the strong positive pressure has been built up in process chamber 22, this valve is opened and closed again in pulsed fashion, resulting in compressed-air pulses through system lines 28, first valve unit 28, and first delivery line 32, and in almost complete, or complete, emptying of system line 28. As a result of this pulsed opening and closing of the valve unit (not depicted), the reagent is blown in pulsed fashion, together with air, through terminating opening 33 of delivery line 32 into first reagent container 24. Because terminating opening 33 of delivery line 32 is located above maximum fill level 35 of reagent container 24, however, this does not result in the formation of bubbles within the reagent, thereby minimizing or decreasing any splashing out of reagent as compared with an apparatus in which only one line is provided for filling and emptying the reagent, the terminating opening of said line being located below maximum fill level 35 of the reagent in first reagent container 24.

As an alternative to first valve unit 26 that opens and closes as a result of the negative or positive pressure in process chamber 22, it is also possible to provide a controllable valve unit that, as a function of a control signal, respectively suppresses or enables communication between system line 28 and first suction line 30, or system line 28 and delivery line 32.

Figure 2:
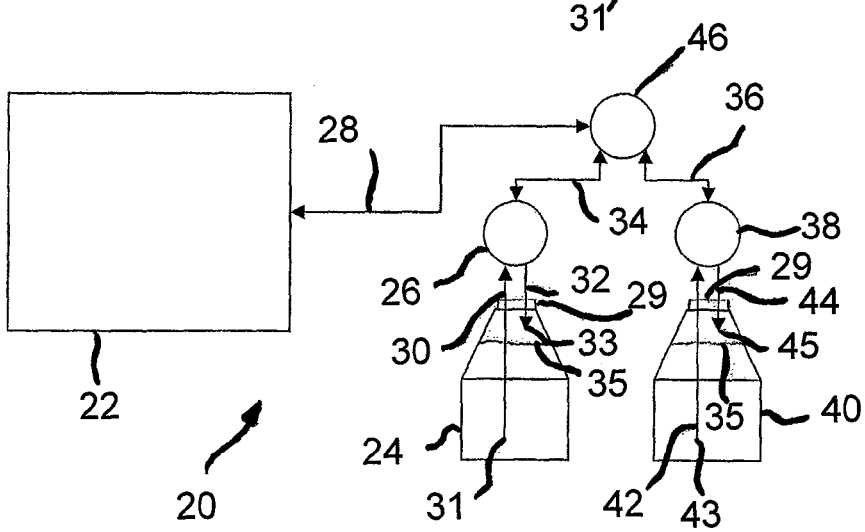
FIG. 2 is a block diagram of a second embodiment of the tissue processor.

FIG. 2 is a block diagram of an embodiment of tissue processor 20 in which, in contrast to the embodiment shown in FIG. 1, a second reagent container 40, a second suction line 42 having a terminating opening 43 of second suction line 42, a second delivery line 44 having a terminating opening 45 of second delivery line 44, and a second valve unit 38 are additionally arranged. A control valve, in particular a rotary valve 46, is furthermore additionally provided, which valve in a first index position of rotary valve 46 enables communication between system line 28 and a first sub-system line 34 and suppresses communication between system line 28 and a second sub-system line 36, and in a second index position of rotary valve 46 suppresses communication between system line 28 and first sub-system line 34, and enables communication between system line 28 and second sub-system line 36.

First sub-system line 34 is coupled to first valve unit 26 in such a way that with rotary valve 46 in the first valve position, communication between process chamber 22 and first reagent container 24 is possible. With rotary valve 46 in the first valve position, the manner of operation of the embodiment shown in FIG. 2 corresponds to the manner of operation of the embodiment shown in FIG. 1.

Second sub-system line 36 is coupled to second valve unit 38 so that with rotary valve 46 in the second valve position, communication between process chamber 22 and second reagent container 40 is enabled. The construction and manner of operation of second valve unit 38 with second suction line 42 and second delivery line 44 correspond to the manner of operation of first valve unit 26 with first suction line 30 and first delivery line 32. In contrast to the first exemplifying embodiment, however, it is possible to switch between the two valve units 26, 38 and reagent containers 24, 40 with the aid of rotary valve 46. Identical or similar reagents can be stocked in the two reagent containers 24 and 40. For example, identical reagents of different levels of purity, or entirely different reagents, can be stocked in the two containers 24, 40 for different process steps for processing the tissue specimens. For example, a dehydration reagent can be stocked in first reagent container 24 and a clearing reagent in second reagent container 40.

Figure 3:
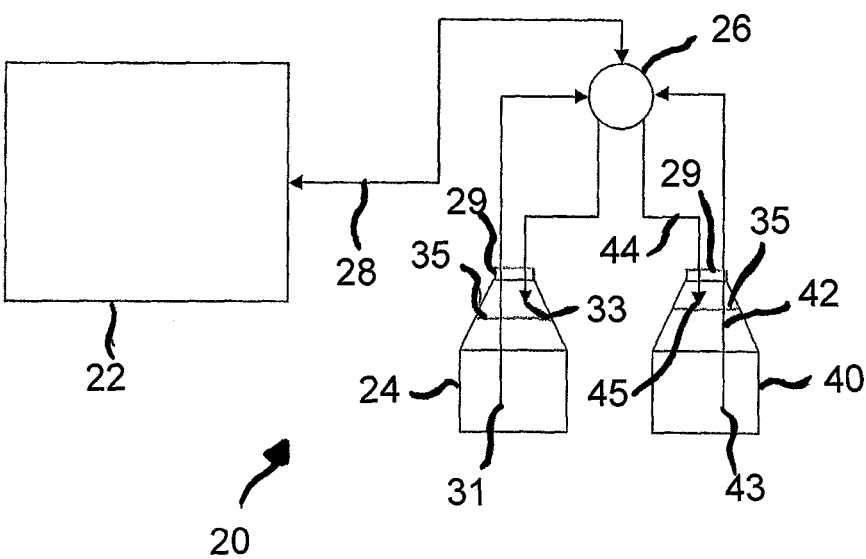
FIG. 3 is a block diagram of a third embodiment of a tissue processor.

FIG. 3 is a block diagram of a third embodiment of tissue processor 20 that basically corresponds in terms of construction and manner of operation to the exemplifying embodiment according to FIG. 1; in contrast thereto, second reagent container 40 is provided with second suction line 42 and with second delivery line 44, and first valve unit 26 correspondingly comprises a further input and a further output for connecting second suction line 42 and second delivery line 44, respectively. In this embodiment as well, the reagents can be removed from the two containers 24, 40 or conveyed back into them, mutually independently, with the aid of positive or negative pressure, respectively, in process chamber 22.

In this embodiment, first valve unit 26 is preferably a controllable valve that, as a function of a control signal, respectively suppresses and enables communication between system line 28 and first reagent container 24 or second reagent container 40.

Figure 4:
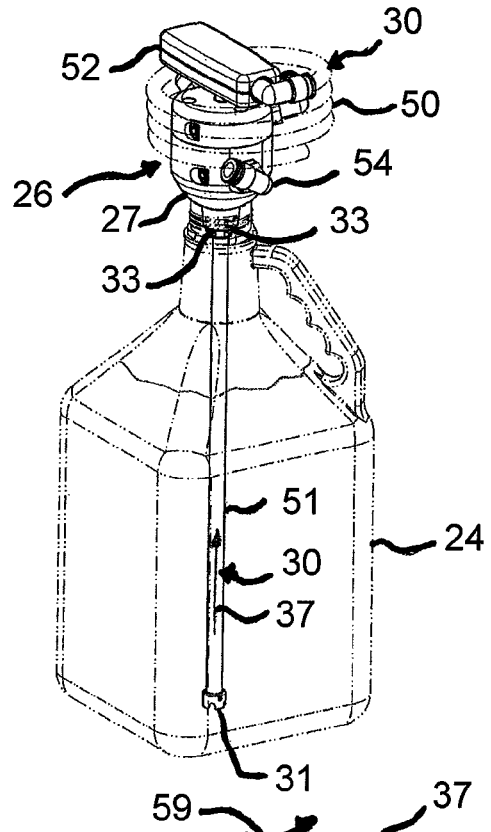
FIG. 4 shows an apparatus for emptying and filling a reagent container, and a reagent container.

FIG. 4 is a perspective depiction of the apparatus for emptying and filling first reagent container 24, first reagent container 24 being depicted with dashed lines. In this exemplifying embodiment, first valve unit 26 is encompassed by a coupling member 27 which is provided in order to couple the apparatus to first reagent container 24. In this connection, coupling member 27 can also be referred to as a connecting member or as a cover, in particular a universal cover for different reagent containers. In other words, first valve unit 26 and cover 29 are combined in coupling member 27.

First valve unit 26 comprises a coupling element 52, a suction connector 54, and a suction spiral 50, which are elements of first suction line 30. Coupling element 52 couples suction spiral 50 to coupling member 27. Suction connector 54 connects the spiral-shaped part of suction line 30, in particular suction spiral 50, to coupling member 27, which in turn couples suction spiral 50 to a lance-shaped part of suction line 30, in particular to a suction lance 51. Suction lance 51 projects a long way into first reagent container 24, so that terminating opening 31 of first suction line 30 is arranged close to the bottom of the first reagent container. It is advantageous in this connection if the length of suction lance 51 is variable, so that the apparatus is adaptable to first reagent containers 24 of different sizes. A suction direction 37 identifies the flow direction in which the reagent is drawn, in particular via suction lance 51, out of first reagent container 24. The aspirated reagent then flows via coupling element 52 into suction spiral 50, and through suction connector 54 into first valve unit 26 of coupling member 27.

Figure 5:
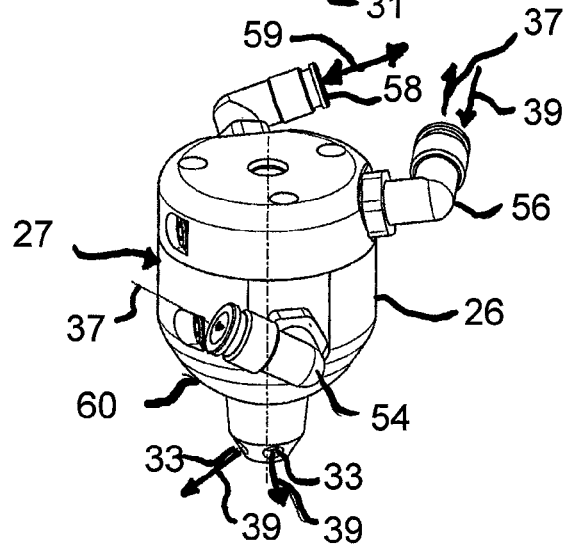
FIG. 5 shows a coupling member.

FIG. 5 shows that coupling member 27 comprises, in addition to suction connector 54, a system line connector 56 for connection to system line 28 and a venting connector 58 for connection to a venting line (not depicted). A venting direction 59 identifies a flow direction of the air that, in order to vent first reagent container 24, can flow into or escape from first reagent container 24. In addition to suction direction 37, which identifies the flow direction of the reagent during the operation of emptying first reagent container 24, a delivery direction 39 identifies the flow direction of the reagent during the operation of filling first reagent container 24, in particular through first delivery line 32 to first reagent container 24. As in FIG. 4, suction direction 37 identifies the flow direction in which the reagent is drawn out of first reagent container 24, in particular through suction connector 54.

Coupling member 27 comprises, at its part that rests on the opening of first reagent container 24 when used as intended, a coupling connector 60 that is preferably embodied in the shape of a spherical segment, enabling sealed placement of coupling member 27 onto a wide variety of openings of reagent containers. Coupling member 27 comprises at least one, preferably several terminating openings 33 of first delivery line 32; delivery direction 39 once again identifies the flow direction of the reagent when the latter is being delivered into first reagent container 24. Terminating openings 33 of first delivery line 32 are preferably arranged close to coupling connector 60, thus ensuring that when used as intended, they are arranged above maximum fill level 35 of reagent container 24. It is advantageous in this connection if the spacing between coupling connector 60 and terminating openings 33 of first delivery line 32 is variable, so that the apparatus is adaptable to maximum fill levels 35 of different heights.

Figure 6:
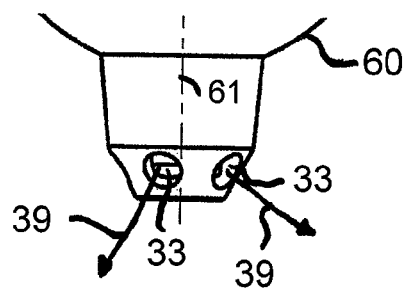
FIG. 6 shows terminating openings of a delivery line.

FIG. 6 is a detail view in accordance with FIG. 5, from which it is evident that terminating openings 33 of first delivery line 32 are embodied and arranged so that when used as intended, delivery direction 39 extends obliquely with reference to a vertical line 61. The formation of splashes and bubbles in first reagent container 24 upon filling of first reagent container 24 is thereby prevented.

Figure 7:
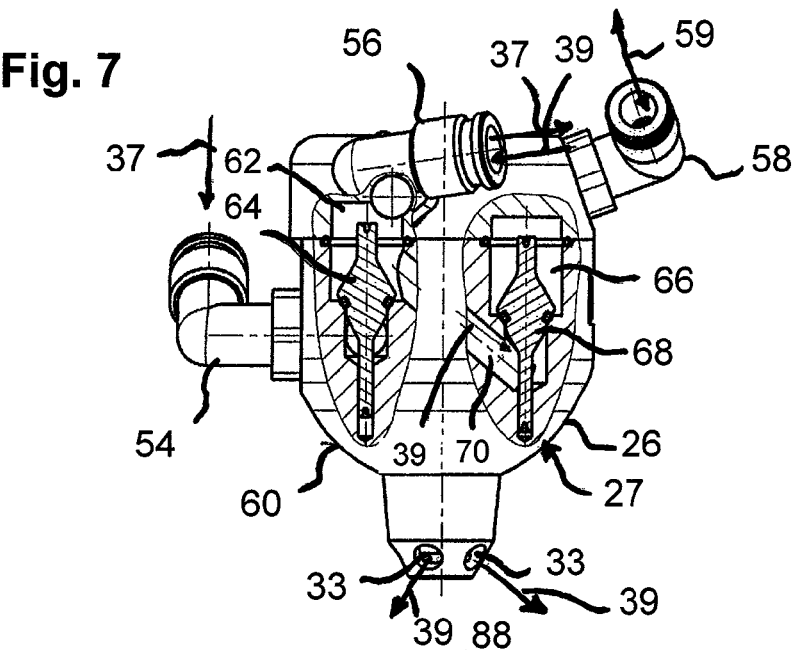
FIG. 7 is a section through the coupling member.

FIG. 7 is a section through first valve unit 26 in coupling member 27. First valve unit 26 comprises a first valve having a first valve chamber 62 and having a first valve plunger 64 that is arranged in first valve chamber 62. In addition, first valve unit 26 comprises a second valve having a second valve chamber 66 and having a second valve plunger 68 that is arranged in second valve chamber 66. First valve chamber 62 communicates with second valve chamber 66 via a valve chamber connection 70. In the depiction of FIG. 7, valve plungers 64, 68 are in their idle state, which is assumed e.g. when no reagent is being aspirated or delivered through first valve unit 26. In the idle state, the two valve plungers 64, 68 assume their closed position, preferably as a result only of the gravity acting on them; this contributes to a low opening pressure for the valves and thereby to rapid filling and emptying of first reagent container 24.

When negative pressure is generated in process chamber 22, first valve unit 26 then moves into its first valve position, in which communication between system line 28 and first suction lines 30 is enabled and communication between system line 28 and first delivery line 32 is suppressed. The negative pressure in process chamber 22 produces, in particular, a negative pressure in system line 28, so that the reagent is drawn through suction lance 51, suction spiral 50, and suction connector 54 in suction direction 37 into first valve chamber 62, with the result that first valve plunger 64 rises and moves out of its closed position into its open position. The negative pressure acting via system connector 56 in suction direction 37 furthermore causes second valve plunger 68 to be pushed into its closed position.

When a positive pressure is generated in process chamber, first valve unit 26 then moves into its second valve position, in which communication between system line 28 and first delivery line 32 is enabled and communication between system line 28 and first suction line 30 is suppressed. In particular, the positive pressure in process chamber 22 causes the reagent to be delivered through system line 28 and, in delivery direction 39, through system line connector 56 into first valve chamber 62. This causes first valve plunger 64 to remain in its closed position, but to be impinged upon additionally with a force in a closing direction. The reagent flows through valve chamber connection 70 into second valve chamber 66, where it lifts second valve plunger 68 out of its closed position so that the reagent flows through second valve chamber 66 to terminating openings 33 of first delivery line 32.

Figure 8:
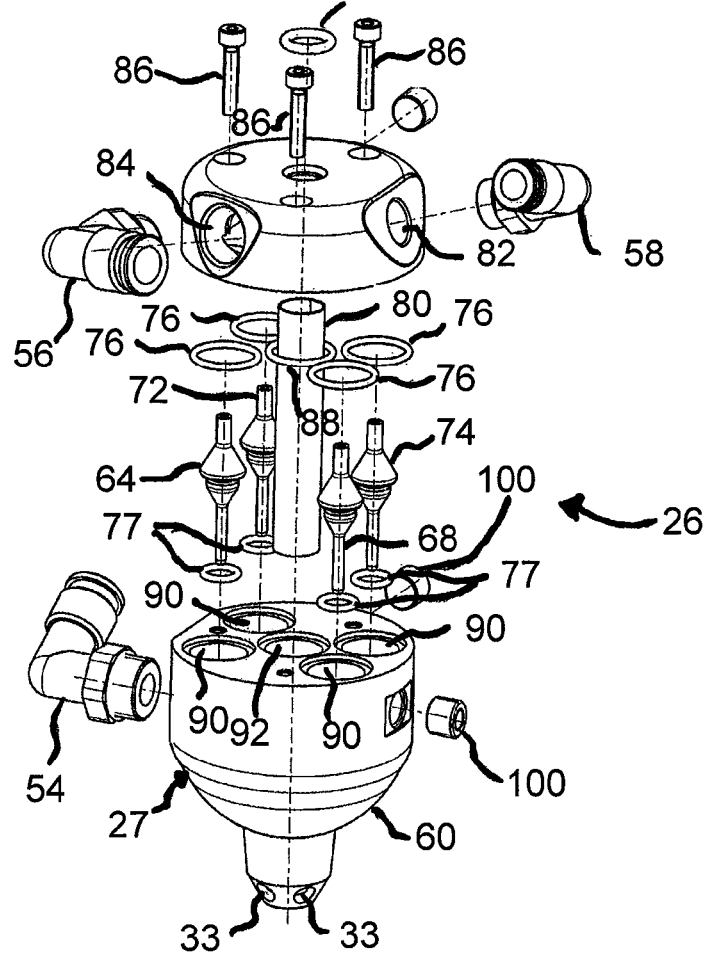
FIG. 8 is an exploded depiction of the coupling member with the valve unit.

FIG. 8 is an exploded depiction of valve body 26. The exploded view shows a third valve plunger 72 and a fourth valve plunger 74 that are elements of a third and fourth valve, respectively. The third valve is arranged redundantly with respect to the first valve, and the fourth valve redundantly with respect to second valve 68. In other words, the arrangement shown in a sectioned depiction in FIG. 7 is present in duplicate inside valve body 26, so that upon failure of one of the valves a second valve can take over its function, so that the functionality of the entire valve unit 26 is ensured even if of one valve fails. As an alternative to this, only the first and the second valve can be provided.

Valve plungers 64, 68, 72, 74 are preferably wedge-shaped or double-wedge-shaped. This contributes to the ability of the reagent to flow past valve plungers 64, 68, 72, 74 with little flow resistance. This contributes to rapid emptying and filling of first reagent container 24, and thus of process chamber 22, under relatively little suction and pressure, respectively. Valve plungers 64, 68, 72, 74 are preferably sealed via first sealing rings 77 in the direction toward first reagent container 24, and by means of second sealing rings 77 in the direction away from first reagent container 24. Mounting means 86 serve to connect an upper part of first valve unit 26 fixedly to a lower part of first valve unit 26 after valve plungers 64, 68, 72, 74 and first and second sealing rings 76, 77 have been put in place. Before closure of the two parts of the first valve unit, valve plungers 64, 68, 72, 74 are placed into corresponding valve chamber openings 90, in particular of first valve chamber 62 and of second valve chamber 66.

Arranged centrally within first valve unit 26 is a venting tube 80 that communicates with venting connector 58, venting connector 58 being arranged on first valve body 26 via a venting connector opening 82. In the same fashion, system line connector 56 is coupled via a system connector opening 84 to first valve unit 26. A central sealing ring 88 seals venting tube 80 with respect to first valve body 26. Venting tube 80 is arranged in a delivery line orifice 92 that is part of first delivery line 32. First suction line 30, in particular the lance-shaped part of the first suction line, is preferably guided through venting tube 80. The reagent is thus guided, via first suction line 30, centrally through first valve unit 26. Air for venting first reagent container 24 is guided between the outer wall of suction line 30 and the inner wall of venting tube 80, and the reagent is delivered into first reagent container 24 between an outer wall of venting tube 80 and an inner wall of delivery line orifice 92. Venting tube 80 can be fastened in first valve unit 26 with the aid of fastening apparatuses 100.

Figure 9:
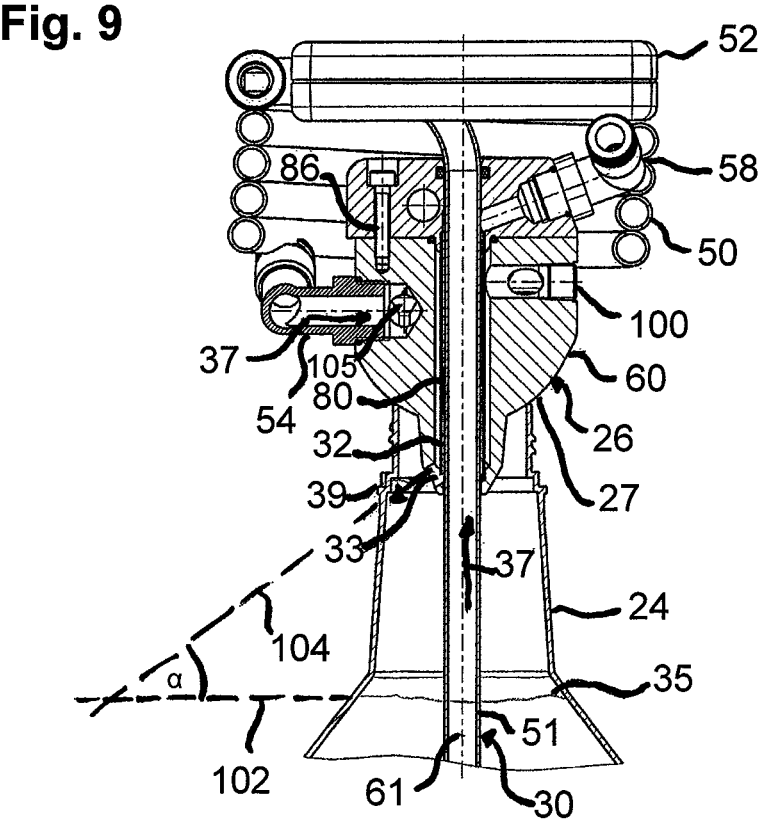
FIG. 9 is a section through the coupling member on the reagent container.

FIG. 9 shows a further section through the first valve unit, from which it is apparent that in addition to the elements explained in connection with the Figures recited previously, there is embodied in first valve unit 26 a bypass 105, in particular a bypass orifice, which couples suction spiral 50 via suction connector 54 to the upper part (shown in FIG. 7) of first valve chamber 62, in particular independently of the position of first valve plunger 64. It is essential in this context that an opening cross section of bypass 105 be substantially smaller than the opening cross section of first suction line 30 and of first delivery line 32. In other words, a permanent leak or an unsealed valve is produced by bypass 105. This causes suction spiral 50 to be emptied, in particular, when air is delivered in pulsed fashion through first delivery line 32, thereby preventing carryover and contamination of the reagent. As an alternative thereto, bypass 105 can also connect suction spiral 50 to first delivery line 32.

FIG. 9 further shows that an axis 104 of first delivery line 32, in the region of latter's terminating opening 33, encloses with a horizontal line 102 an angle that is between 0° and 90°. This means that axis 104 is arranged obliquely with reference to vertical line 61.

Figure 10:
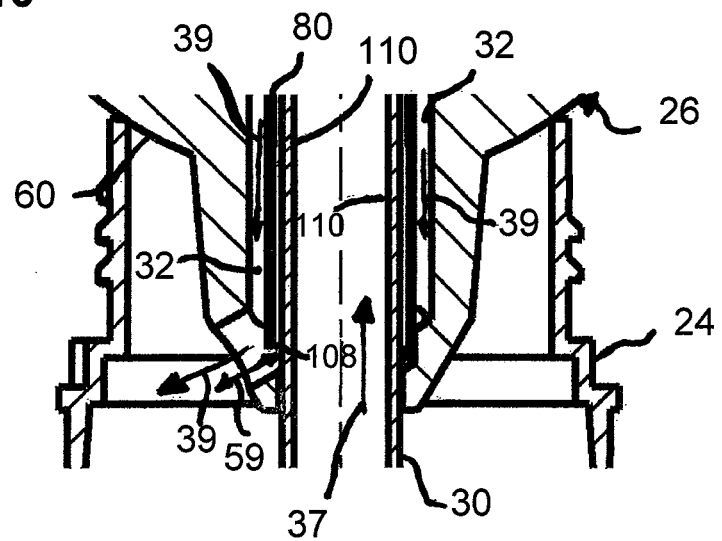
FIG. 10 is a detail view in accordance with FIG. 9.

FIG. 10 is a detail view in accordance with FIG. 9, indicating on the one hand flow directions 39, 37 of the reagent through first delivery line 32 and first suction line 37, respectively, and also venting directions 59 and thus the flow direction of the air for venting first reagent container 24. A lower terminating opening 108 of a venting line 110 defined by venting tube 80 and first suction line 30 is located inside terminating opening 33 of first delivery line 32, specifically directly below the transition of first delivery line 32 into its terminating opening 33. This produces a particularly rapid pressure dissipation in particular when the reagent is being forced in pulsed fashion into first reagent container 24, and thus prevents spraying of the reagent. Terminating opening 108 of venting line 110 is thus arranged between terminating opening 33 of first delivery line 32 and terminating opening 31 of first suction line 30, in particular close to terminating opening 33 of first delivery line 32.

As an alternative to first valve unit 26 that is depicted, which is encompassed by coupling member 27, coupling member 27 and first valve unit 26 can be divided into two members that merely communicate via the lines and are otherwise independent. First delivery line 32 can furthermore comprise more or fewer terminating openings 33. In addition to the first and the second reagent container 24, 40, further reagent containers can be provided. Each of the reagent containers can be coupled to an apparatus, explained previously, for filling and emptying the corresponding reagent container. The apparatuses can be elements of tissue processor 20 or can be independent thereof.

The invention is not to be limited to the specific embodiments disclosed, and modifications and other embodiments are intended to be included within the scope of the invention.

LIST OF REFERENCE NUMERALS

20 Tissue processor
22 Process chamber
24 First reagent container
26 First valve unit
27 Coupling member
28 System line
29 Cover
30 First suction line 31 Terminating opening of first suction line
32 First delivery line
33 Terminating opening of first delivery line
34 First sub-system line
35 Maximum fill level
36 Second sub-system line
37 Suction direction
38 Second valve unit
39 Delivery direction
40 Second reagent container
42 Second suction line
43 Terminating opening of second suction line
44 Second delivery line
45 Terminating opening of second delivery line
46 Rotary valve
50 Suction spiral
51 Suction lance
52 Coupling element
54 Suction connector
56 System line connector
58 Venting connector
59 Venting direction
60 Coupling connector
61 Vertical line
62 First valve chamber
64 First valve plunger
66 Second valve chamber
68 Second valve plunger
70 Valve chamber connection
72 Third valve plunger
74 Fourth valve plunger
76 First sealing rings
77 Second sealing rings
80 Venting tube
82 Venting connector opening
84 System connector opening
86 Mounting means
88 Central sealing ring
90 Valve chamber openings
92 Delivery line orifice
100 Fastening apparatus
105 Bypass
108 Terminating opening of venting line
110 Venting line

What is claimed is:

1. An apparatus for safety-compliant emptying and filling of a reagent container (24, 40) for a tissue processor (20), comprising:
   a suction line (30, 42) for aspirating a reagent out of the reagent container (24, 40), the suction line (30, 42) having a terminating opening (31, 43);
   a delivery line (32, 44) for filling the reagent container (24) with the reagent, the delivery line (32, 44) having a plurality of terminating openings (33, 45);
   the terminating opening (31, 43) of the suction line (30, 42) being spaced away from at least one of the plurality of terminating openings (33, 45) of the delivery line (32, 44);
   a system line (28, 34, 36) for communication with a process chamber (22) of the tissue processor (20); and
   a valve unit (26, 38) communicating with the system line (28, 34, 36);
   wherein the valve unit (26, 38) in a first valve setting enables communication between the system line (28, 34, 36) and the suction line (30, 42) and suppresses communication between the system line (28, 34, 36) and the delivery line (32, 44), and wherein the valve unit (26, 38) in a second valve setting enables communication between the system line (28, 34, 36) and the delivery line (32, 44) and suppresses communication between the system line (28, 34, 36) and the suction line (30, 42).

2. The apparatus according to claim 1, further comprising a coupling member (27) for coupling the apparatus to the reagent container (24, 40), wherein the coupling member (27) is spaced from the terminating opening (31, 43) of the suction line (30, 42) by a first spacing and the coupling member (27) is spaced from the terminating opening (33, 45) of the delivery line (32, 44) by a second spacing; and
   wherein the first spacing is greater than the second spacing.

3. The apparatus according to claim 2, wherein at least one of the first and second spacings is variable.

4. The apparatus according to claim 1, wherein the valve unit (26, 38) includes at least two valves.

5. The apparatus according to claim 1, wherein the valve unit (26, 38) includes at least four valves, wherein two of the valves are arranged redundantly.

6. The apparatus according to claim 4, wherein at least one of the valves comprises a wedge-shaped or double-wedge-shaped valve plunger (64, 68, 72, 74).

7. The apparatus according to claim 4, wherein the valves have an idle state in which the valves are closed.

8. The apparatus according to claim 7, wherein the valves are arranged such that gravity positions the valves in the idle state.

9. The apparatus according to claim 1, further comprising:
   a coupling member (27) for coupling the apparatus to the reagent container (24, 40), wherein the coupling member (27) is spaced from the terminating opening (31, 43) of the suction line (30, 42) by a first spacing and the coupling member (27) is spaced from the terminating opening (33, 45) of the delivery line (32, 44) by a second spacing;
   wherein the first spacing is greater than the second spacing; and
   wherein the valve unit (26, 38) is encompassed by the coupling member (27).

10. The apparatus according to claim 1, wherein the suction line (30, 42) is lance-shaped at least in part.

11. The apparatus according to claim 1, wherein the suction line (30, 42) is spiral-shaped at least in part.

12. The apparatus according to claim 11, further comprising a bypass (105) that enables communication between the spiral-shaped part of the suction line (30, 42) and the delivery line (32, 44), the bypass (105) comprising at least one constriction whose opening cross section is smaller than an opening cross section of the suction line (30, 42) and smaller than an opening cross section of the delivery line (32, 44).

13. The apparatus according to claim 3, wherein the coupling member (27) encompasses the terminating opening (33, 45) of the delivery line (32, 44).

14. The apparatus according to claim 1, further comprising a venting line (110) for controlling pressure in the reagent container, the venting line (110) having a terminating opening (108).

15. The apparatus according to claim 14, further comprising:
   a coupling member (27) for coupling the apparatus to the reagent container (24, 40), wherein the coupling member (27) is spaced from the terminating opening (31, 43) of the suction line (30, 42) by a first spacing and the coupling member (27) is spaced from the terminating opening (33, 45) of the delivery line (32, 44) by a second spacing;

wherein the first spacing is greater than the second spacing; and wherein the coupling member (27) at least in part encompasses the venting line (110) and the terminating opening (108) of the venting line (110).

16. The apparatus according to claim 15, wherein the terminating opening (108) of the venting line (110) is arranged between the terminating opening (31, 43) of the suction line (30, 42) and the terminating opening (33, 45) of the delivery line (32, 44).

17. The apparatus according to claim 15, wherein the terminating opening (108) of the venting line (110) is arranged directly next to the terminating opening (33, 45) of the delivery line (32, 44).

18. The apparatus according to claim 1, wherein in a region of the terminating openings (33) of the delivery line (32, 44), the delivery line (32, 44) is arranged obliquely with respect to a surface of the reagent in the reagent container (24, 40).

19. An apparatus for safety-compliant emptying and filling of a reagent container (24, 40) for a tissue processor (20), comprising:
- a suction line (30, 42) for aspirating a reagent out of the reagent container (24, 40), the suction line (30, 42) having a terminating opening (31, 43), wherein the suction line (30, 42) is spiral-shaped at least in part;
- a delivery line (32, 44) for filling the reagent container (24) with the reagent, the delivery line (32, 44) having a plurality of terminating openings (33, 45);
- the terminating opening (31, 43) of the suction line (30, 42) being spaced away from at least one of the plurality of terminating openings (33, 45) of the delivery line (32, 44); and
- a bypass (105) that enables communication between the spiral-shaped part of the suction line (30, 42) and the delivery line (32, 44), the bypass (105) comprising at least one constriction whose opening cross section is smaller than an opening cross section of the suction line (30, 42) and smaller than an opening cross section of the delivery line (32, 44).

20. An apparatus for safety-compliant emptying and filling of a reagent container (24, 40) for a tissue processor (20), comprising:
- a suction line (30, 42) for aspirating a reagent out of the reagent container (24, 40), the suction line (30, 42) having a terminating opening (31, 43);
- a delivery line (32, 44) for filling the reagent container (24) with the reagent, the delivery line (32, 44) having a plurality of terminating openings (33, 45);
- the terminating opening (31, 43) of the suction line (30, 42) being spaced away from at least one of the plurality of terminating openings (33, 45) of the delivery line (32, 44);
- a venting line (110) for controlling pressure in the reagent container, the venting line (110) having a terminating opening (108);
- a coupling member (27) for coupling the apparatus to the reagent container (24, 40), wherein the coupling member (27) is spaced from the terminating opening (31, 43) of the suction line (30, 42) by a first spacing and the coupling member (27) is spaced from the terminating opening (33, 45) of the delivery line (32, 44) by a second spacing;
- wherein the first spacing is greater than the second spacing; and
- wherein the coupling member (27) at least in part encompasses the venting line (110) and the terminating opening (108) of the venting line (110).

* * * * *